United States Patent
Abe

(10) Patent No.: US 9,857,215 B2
(45) Date of Patent: Jan. 2, 2018

(54) OBJECT INFORMATION ACQUIRING APPARATUS

(71) Applicant: CANON KABUSHIKI KAISHA, Tokyo (JP)

(72) Inventor: Naoto Abe, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 314 days.

(21) Appl. No.: 14/644,531

(22) Filed: Mar. 11, 2015

(65) Prior Publication Data

US 2015/0268091 A1 Sep. 24, 2015

(30) Foreign Application Priority Data

Mar. 19, 2014 (JP) .................................. 2014-056892

(51) Int. Cl.
*G01R 31/28* (2006.01)
*G01H 11/06* (2006.01)
(Continued)

(52) U.S. Cl.
CPC ........... *G01H 11/06* (2013.01); *A61B 5/0095* (2013.01); *A61B 5/4312* (2013.01);
(Continued)

(58) Field of Classification Search
CPC .......... G01R 31/2834; G01R 31/31705; G01R 31/31707; G01R 31/3183; G01R 31/318307

See application file for complete search history.

(56) References Cited

U.S. PATENT DOCUMENTS 4,689,499 A * 8/1987 Yee ..................... G01R 19/1659
326/62
6,018,239 A * 1/2000 Berkcan ............... G01R 15/181
324/127
(Continued)

FOREIGN PATENT DOCUMENTS

JP 2009-165931 7/2009
JP 2011-183057 9/2011
(Continued)

OTHER PUBLICATIONS

Extended European Search Report issued Aug. 12, 2015 in EPA 15159561.8 (in English).

*Primary Examiner* — Tung X Nguyen
*Assistant Examiner* — Dominic Hawkins
(74) *Attorney, Agent, or Firm* — Fitzpatrick, Cella, Harper & Scinto

(57) ABSTRACT

An object information acquiring apparatus includes a detector including m-number of probes to which a voltage is supplied and a current/voltage conversion circuit which converts a current into a voltage, a receiver processing electric signals from the probes, and a relay board respectively relaying power distribution lines between the electrical power source and the probes and signal wirings between the receiver and the probe, wherein the relay board receives input of signal wirings and power distribution lines from n-number (m≥n) of probes among the m-number of probes, connects the signal wirings from the n-number of probes to the receiver, and connects, to the electrical power source side, the power distribution lines of a number that is fewer than the power distribution lines from the n-number of probes.

14 Claims, 11 Drawing Sheets

(51) Int. Cl.
  *A61B 8/08*     (2006.01)
  *A61B 8/13*     (2006.01)
  *A61B 5/00*     (2006.01)
  *H04R 3/00*     (2006.01)
  *H04R 23/00*    (2006.01)
  *A61B 8/00*     (2006.01)

(52) U.S. Cl.
  CPC .............. *A61B 8/0825* (2013.01); *A61B 8/13* (2013.01); *A61B 8/56* (2013.01); *H04R 3/00* (2013.01); *H04R 23/008* (2013.01); *A61B 8/4477* (2013.01); *A61B 8/4494* (2013.01); *A61B 2560/0214* (2013.01); *H04R 2420/00* (2013.01)

(56) References Cited

U.S. PATENT DOCUMENTS

| | | | | |
|---|---|---|---|---|
| 6,211,513 B1* | 4/2001 | Brown | ................... | G01R 27/18 19/0.21 |
| 2005/0159024 A1* | 7/2005 | Yamada | ................. | H05K 1/144 439/64 |
| 2008/0242979 A1* | 10/2008 | Fisher | .................. | A61B 6/4233 600/427 |
| 2008/0273424 A1 | 11/2008 | Wodnicki et al. | ............. | 367/180 |
| 2009/0252024 A1* | 10/2009 | Maeda | ................... | B82Y 10/00 369/126 |
| 2010/0165846 A1* | 7/2010 | Yamaguchi | ........ | H04B 7/15592 370/236 |
| 2010/0187664 A1* | 7/2010 | Polhemus | ............. | H01L 23/495 257/666 |
| 2010/0279342 A1* | 11/2010 | Kijima | ..................... | G01N 1/06 435/40.52 |
| 2011/0224532 A1* | 9/2011 | Tanabe | ................. | A61B 5/0091 600/407 |
| 2011/0306865 A1 | 12/2011 | Thornton et al. | ............ | 600/407 |
| 2012/0083683 A1* | 4/2012 | Kuwabara | ............ | A61B 5/0507 600/407 |
| 2012/0306802 A1* | 12/2012 | McCracken | .......... | G06F 3/0416 345/174 |
| 2013/0023767 A1* | 1/2013 | Mammone | .......... | A61B 8/0825 600/440 |
| 2013/0312526 A1 | 11/2013 | Oishi | ............................... | 73/620 |

FOREIGN PATENT DOCUMENTS

JP     2012-179348        9/2012
WO    WO 2010/030817 A   3/2010

* cited by examiner

OBJECT INFORMATION ACQUIRING APPARATUS

BACKGROUND OF THE INVENTION

Field of the Invention

The present invention relates to an object information acquiring apparatus. The present invention particularly relates to a technique of mounting an electric circuit including a detector which uses a CMUT probe.

Description of the Related Art

In recent years, research and development of photoacoustic imaging apparatuses which image the inside of a living body using the photoacoustic effect are being conducted. A photoacoustic imaging apparatus applies a pulsed laser beam (laser pulse), which is emitted for a short period, inside the living body, and generates an image from the ultrasound waves (photoacoustic waves) that are generated, during the volume expansion caused by the heat generation, by the biological tissues that absorbed the energy of the pulsed laser beam. A photoacoustic imaging apparatus is undergoing research and development, for example, as a device for observing a person's breast for the early detection of breast cancer.

For detecting the ultrasound waves (photoacoustic waves), a capacitive micromachined ultrasound transducer (CMUT), which is a micro functional element that is manufactured with the micro-machining technique, is being used (for example, Japanese Patent Application Laid-open No. 2011-183057). A CMUT is also referred to as a capacitance-type transducer, and is undergoing research as a replacement of a piezoelectric element. When a CMUT is used, it is possible to send and receive ultrasound waves based on the vibration of a vibration membrane, and in particular superior broadband characteristics are exhibited in a liquid. Accordingly, not only can a CMUT be used for detecting photoacoustic waves, it can also be used for sending ultrasound waves and detecting echo waves. Details regarding a CMUT element are described in Japanese Patent Application Laid-open No. 2009-165931).

Meanwhile, thermal acoustic-type scanning devices which generate images from acoustic waves associated with the thermal expansion in the biological tissues caused by the electromagnetic radiation pulse are also being researched and developed. A thermal acoustic-type scanning device is also undergoing research and development, for example, as a device for observing a person's breast for the early detection of breast cancer (for example, US Patent Application Publication No. 2011/0306865). US Patent Application Publication No. 2011/0306865 discloses a thermal acoustic-type scanning device having a detector in which a plurality of ultrasound transducers are arranged on a container having a spherical surface.

Patent Literature 1: Japanese Patent Application Laid-open No. 2011-183057
Patent Literature 2: US Patent Application Publication No. 2011/0306865
Patent Literature 3: Japanese Patent Application Laid-open No. 2009-165931
Patent Literature 4: Japanese Patent Application Laid-open No. 2012-179348

SUMMARY OF THE INVENTION

As described above, Japanese Patent Application Laid-open No. 2011-183057 uses a capacitive micromachined ultrasound transducer element (CMUT element) for detecting ultrasound waves (photoacoustic waves). Nevertheless, Japanese Patent Application Laid-open No. 2011-183057 makes no description concerning a converter for converting the capacitance change of a capacitive micromachined ultrasound transducer element (CMUT element) into a voltage change. When converting a minute capacitance change of the capacitive micromachined ultrasound transducer element (CMUT element) into a voltage change, the converter needs to be mounted near the CMUT element in order to improve the signal noise ratio (SNR). Consequently, in addition to the signal lines, the power distribution lines also need to be wired up to the converter near the CMUT element.

Note that, in the ensuing explanation, the converters mounted near the CMUT element are collectively referred to as a CMUT probe. In certain cases a CMUT element and the converters are arranged on a cabinet and referred to as a CMUT probe. When this kind of CMUT probe is used as an ultrasound transducer, the number of power distribution lines will increase in comparison to the case of using a piezoelectric element. When the number of power distribution lines increases, an additional problem arises in that the region that requires wiring will also increase.

This problem where the wiring region increases becomes a major design problem of the device when the number of CMUT probes increases (for example, 50 or more). In particular, when mounting numerous ultrasound transducers on a container-type detector as with US Patent Application Publication No. 2011/0306865, the expansion of the mounting region associated with the increase in the number of power distribution lines becomes a major problem. In addition, in a device having a movable detector, the mechanical resistance during the movement will increase as the number of wirings increases, and there is a problem in that a large output is demanded by an actuator.

The present invention was devised in view of the foregoing problems. An object of this invention is to reduce the number of power distribution lines used in a CMUT probe.

The present invention provides an object information acquiring apparatus, comprising:

a detector including m-number (m is an integer of 2 or more) of probes having a capacitance conversion element (e.g. CMUT element) to which a voltage is supplied from an electrical power source and a current/voltage conversion circuit which converts a current output from the capacitance conversion element into a voltage;

a receiver processing electric signals from the probes; and a relay board respectively relaying power distribution lines between the electrical power source and the probes and signal wirings between the receiver and the probes, wherein the relay board (a) receives input of signal wirings and power distribution lines from n-number (n is an integer of 2 or more; m≥n) of probes among the m-number of probes, (b) connects the signal wirings from the n-number of probes to the receiver, and, (c) connects, to the electrical power source side, the power distribution lines of a number that is fewer than the power distribution lines from the n-number of probes.

According to the present invention, the number of power distribution lines used in a CMUT probe can be reduced.

Further features of the present invention will become apparent from the following description of exemplary embodiments with reference to the attached drawings.

DESCRIPTION OF THE EMBODIMENTS

Figure 1:
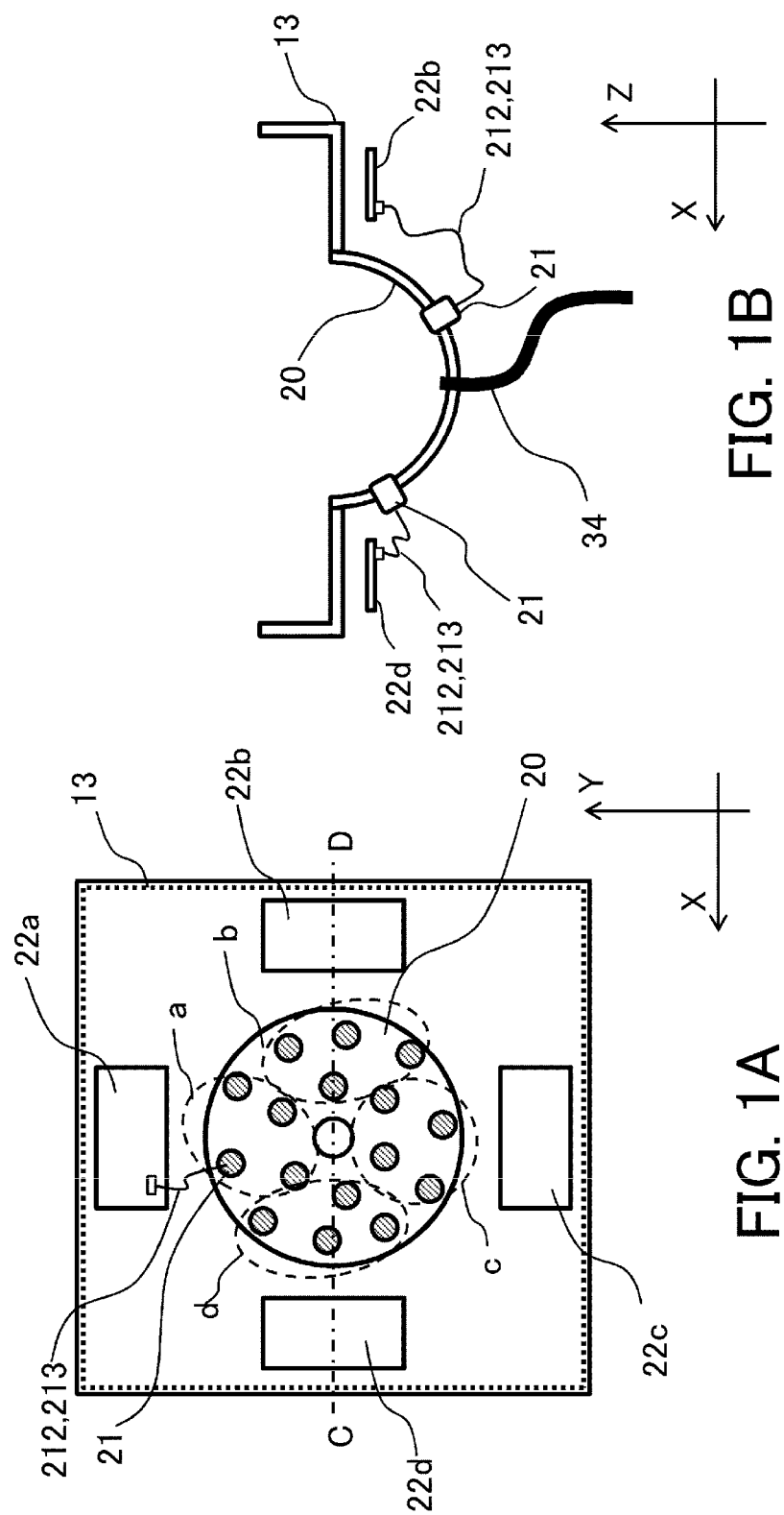
FIGS. 1A and 1B are partial structural diagrams of the photoacoustic imaging apparatus of the first embodiment.

The preferred embodiments of the present invention are now explained with reference to the appended drawings. However, the size, material, shape and relative arrangement of components described below are to be suitably changed depending on the configuration and various conditions of the apparatus to which the present invention is to be applied, and these embodiments are not intended to limit the scope of the present invention to the following descriptions.

The present invention relates to a technology for detecting the acoustic waves that propagate from an object. The detected acoustic waves can be used, among other purposes, for generating characteristic information within the object. Thus, the present invention can also be viewed as an acoustic wave measuring device or its control method, or an acoustic wave measuring method, or an object information acquiring apparatus or its control method, or an object information acquiring method. The present invention can additionally be viewed as a program for causing an information processing device comprising hardware resources such as a CPU to execute the foregoing methods, or a storage medium storing such a program.

The object information acquiring apparatus of the present invention includes a device that uses the photoacoustic tomography technique which applies light (electromagnetic waves) from a light source to an object, and receives (detects) acoustic waves that were generated and propagated at a specified position within the object or on the object surface in accordance with the photoacoustic effect. This kind of object information acquiring apparatus can also be referred to as a photoacoustic device since it can obtain characteristic information within the object as image data or other formats based on photoacoustic measurement. An imaging device including display means such as a display for displaying the image data also falls within the scope of the present invention.

Characteristic information in a photoacoustic device is, for example, emission source distribution of acoustic waves generated based on irradiation of light, initial sound pressure distribution within the object, optical energy absorption density distribution or absorption coefficient distribution derived from the initial sound pressure distribution, or concentration distribution of substances configuring the tissues. Substances configuring the tissues are, for example, blood components of oxygen saturation distribution or oxidation/reduction hemoglobin concentration distribution, or fat, collagen, moisture or the like.

The object information acquiring apparatus of the present invention additionally includes an ultrasound wave device which sends acoustic waves to an object, receives reflected waves (echo waves) that were reflected off at a specified position within the object, and obtains the characteristic information as image data or other formats. Characteristic information in an ultrasound wave device is information that reflects the mode information based on the reflected wave at locations of different acoustic impedances of tissues in the object. The foregoing display means may also display the foregoing ultrasound wave image in an overlapping manner or next to each other.

The acoustic waves in the present invention are typically ultrasound waves, and includes elastic waves referred to as sound waves or acoustic waves. The acoustic waves generated based on the photoacoustic effect are referred to as photoacoustic waves or ultrasound waves. The electric signals converted from acoustic waves with a probe are also referred to as acoustic signals.

(CMUT Probe)

Prior to explaining the details of the embodiments of the present invention, a CMUT probe that is suitable as an ultrasound transducer of a photoacoustic imaging apparatus is explained.

Figure 9A:
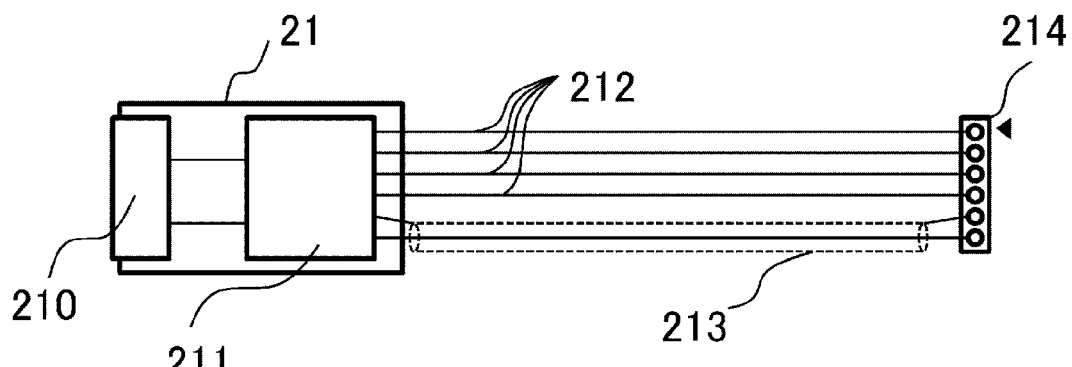
FIGS. 9A and 9B are schematic diagrams explaining the configuration of the CMUT probe and its electric circuit.

FIG. 9A is a schematic diagram explaining the configuration of a CMUT probe. In FIG. 9A, reference numeral 21 is a CMUT probe, and reference numeral 210 is a CMUT element. The CMUT element 210 is a capacitance conversion element. A vibration membrane of the CMUT element 210 is characterized in that it is extremely light and soft compared with an ultrasound transducer realized with a conventional piezoelectric element. Thus, favorable acoustic matching can be realized between the CMUT element-living body without having to use an acoustic matching layer. Thus, broadband signals can be received.

Reference numeral 211 is a current/voltage conversion circuit which converts a capacitance change of a CMUT element into a voltage. Reference numeral 212 is a power distribution line which supplies power to the current/voltage conversion circuit 211 and a bias voltage to the CMUT element. Reference numeral 213 is a signal wiring which outputs the voltage that was converted from the capacitance change of the CMUT element with the current/voltage conversion circuit 211, and for instance is a wiring that uses a coaxial cable. Reference numeral 214 is a connector and a triangular mark shows the position of 1 pin.

The CMUT probe 21 is configured from a CMUT element 210 and a current/voltage conversion circuit 211, and mounted on a cabinet (not shown). In the embodiments of the present invention, as described later, the probe and the relay board are connected via the power distribution line 212, the signal wiring 213 and the connector 214 extending from the CMUT probe 21.

Figure 9B:
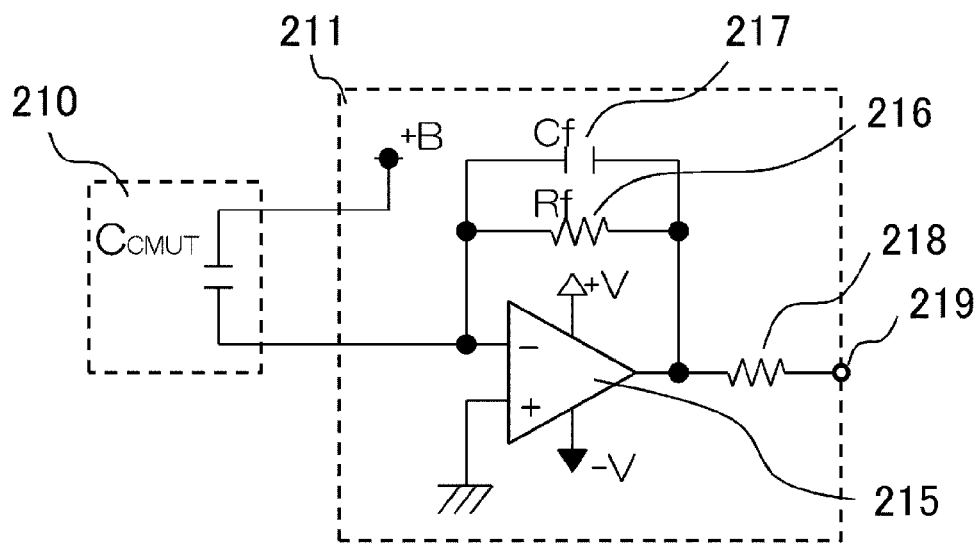

FIG. 9B is a diagram explaining the configuration of the electric circuit of the CMUT probe 21. In FIG. 9B, reference numeral 210 is a CMUT element, and a capacitance is formed with an upper electrode and a lower electrode formed with a thin film. Reference numeral 211 is an expanded and detailed description of the current/voltage conversion circuit. Reference numeral 215 is an operational amplifier, reference numeral 216 is a feedback resistor, reference numeral 217 is a phase compensation capacitor, reference numeral 218 is a resistor that determines the output impedance, and reference numeral 219 is an output terminal of the current/voltage conversion circuit 211.

In FIG. 9B, the CMUT element undergoes a capacitance change in correspondence with the change in the sound pressure of the ultrasound waves. This change in capacity appears as a change in the charge between the upper electrode and the opposite lower electrode by applying a bias voltage to the upper electrode. The bias voltage that is applied is a high voltage of roughly 100 V in order to increase the sensitivity of the CMUT element. By converting this change in charge, or current change, into a voltage change with the current/voltage conversion circuit 211, it is possible to convert the sound pressure of the ultrasound waves into a voltage and output the voltage from the output terminal 219. An output signal of the CMUT probe 21 is output by the signal wiring 213 connected to the output terminal 219.

Here, the CMUT element 210 and the current/voltage conversion circuit 211 are preferably mounted as close to each other as possible. Since this will reduce the stray capacitance (not shown) between the negative input terminal of the operational amplifier 215 and the ground potential, a high band, high sensitivity ultrasound transducer can be realized. Moreover, if there is any stray capacitance between the negative input terminal of the operational amplifier 215 and the noise source (not shown), the operational amplifier 215 amplifies the noise, and the SNR will deteriorate considerably. In order to improve the SNR also, the CMUT element 210 and the current/voltage conversion circuit 211 need to be mounted as close to each other as possible so that the stray capacitance between the negative input terminal of the operational amplifier 215 and the noise source (not shown) is reduced as much as possible.

By mounting the CMUT element 210 and the current/voltage conversion circuit 211 as close to each other as possible in a CMUT probe, it is possible to obtain a relatively large signal amplitude that is broadband and has a favorable SNR compared with an ultrasound transducer that uses a piezoelectric element. Consequently, high quality image reconstruction is enabled.

Meanwhile, compared with a piezoelectric element, since the current/voltage conversion circuit 211 needs to be mounted near the CMUT element 210 in the CMUT probe 21, a power distribution line 212 is required and the number of wirings will increase. In addition, the bias voltage of the CMUT element is a high voltage of roughly 100 V as described above. Thus, among the power distribution lines 212, a highly pressure-resistant wiring is particularly required for the wiring that supplies the bias voltage, and a thick wiring is required compared with the signal wiring 213.

Figure 10:
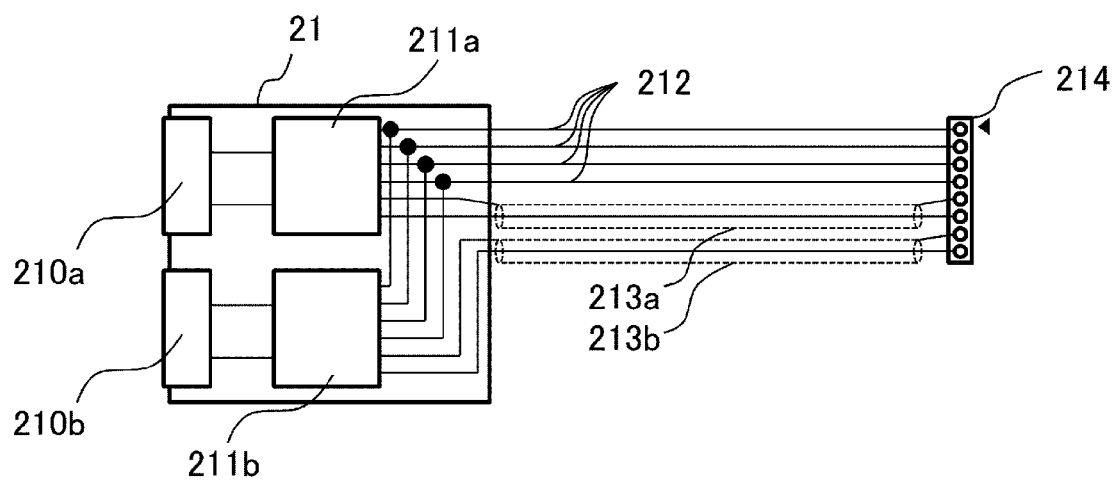
FIG. 10 is a schematic diagram explaining another configuration of the CMUT probe.

Another embodiment of the CMUT probe is now explained. FIG. 10 is a schematic diagram explaining another configuration of the CMUT probe. In FIG. 10, reference numeral 21 is a CMUT probe, and reference numerals 210a, 210b are CMUT elements. Reference numerals 211a, 211b are current/voltage conversion circuits, and each converts a capacitance change of the CMUT elements 210a, 210b into a voltage. Reference numeral 212 is a power distribution line, and supplies power to the current/voltage conversion circuits 211a, 211b and supplies a bias voltage to the CMUT elements 210a, 210b. Reference numerals 213a, 213b are signal wirings, and output the voltage converted from the capacitance change of the CMUT elements 210a, 210b with the current/voltage conversion circuits 211a, 211b. The signal wiring 213 is configured, for instance, from a coaxial cable. Reference numeral 214 is a connector, and a triangular mark shows the position of 1 pin.

The CMUT elements 210a, 210b and the current/voltage conversion circuits 211a, 211b are configured in the same manner as the CMUT element 210 and the current/voltage conversion circuit 211 described above. In FIG. 10, there are two current/voltage conversion circuits 211a, 211b and signal wirings 213a, 213b relative to two CMUT elements 210a, 210b, and only the power distribution line 212 is shared. Even with this kind of configuration, there is no difference other than that two CMUT elements 210a, 210b are mounted on one CMUT probe 21. FIG. 10 shows a mode where two CMUT elements 210a, 210b are mounted on the CMUT probe 21. However, the effect of the present invention can still be yielded even when a greater number of CMUT elements are mounted on one CMUT probe.

Note that, in a CMUT, a vibration membrane that is supported in a vibratable manner and the unit including the first and second electrodes provided by sandwiching a void are referred to as a cell. In addition, there are cases where one CMUT element includes a plurality of cells that have a common electrode as its constituent element and which are electrically connected. In the present specification, one CMUT element may include a plurality of cells that are electrically connected. Moreover, as shown in FIG. 9A and FIG. 10, a plurality of elements may be included in one probe.

As explained above, with the CMUT probe 21, the CMUT element 210 and the current/voltage conversion circuit 211 are mounted close to each other, and a relatively large signal amplitude that is broadband and has a favorable SNR is obtained by reducing the stray capacitance of the negative input terminal of the operational amplifier 215. To put it differently, it is not easy to mount the CMUT element 210 and the current/voltage conversion circuit 211 by separating their distance. Thus, the CMUT probe 21 is an effective mounting mode upon realizing a detector in which ultrasound transducers are mounted by separately them at a relatively large gap (5 mm or more) as described above.

(Structure of Portion Observed with Photoacoustic Imaging Apparatus)

Next, the configuration of a device in the case of applying the present invention to photoacoustic imaging of breasts is explained. However, the present invention is not limited to the observation of breasts, and, as the object, other segments of a living body or a non-living material such as a phantom may also be used. Moreover, the present invention may also be applied to measuring ultrasound wave echoes without limitation to photoacoustic imaging.

Figure 11A:
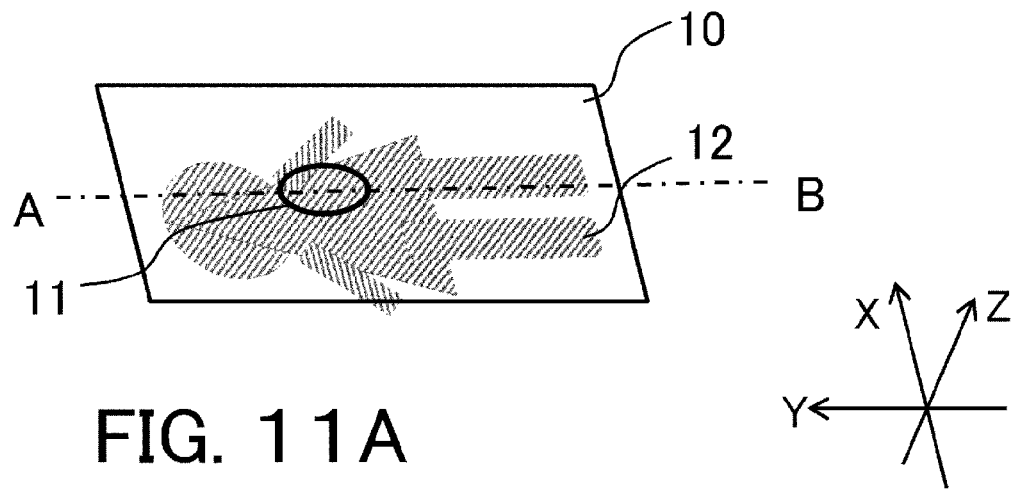
FIGS. 11A and 11B are schematic diagrams showing the examination table and the partial structure of the photoacoustic imaging apparatus.

FIG. 11A is a schematic diagram for facilitating the understanding of the examination table and the patient's position during observation. In FIG. 11A, the patient's horizontal direction is the X axis, craniocaudal direction is the Y axis, and ventrodorsal direction is the Z axis. In FIG. 11A, reference numeral 10 is an examination table, reference numeral 11 is a detection window provided to the examination table 10, and reference numeral 12 is a mark showing the patient's position on the examination table. The embodiments of the present invention show an example of a photoacoustic imaging apparatus which observes a breast in a prone position, but the present invention can also be suitably applied to other methods of observation such as in a sitting position.

Figure 11B:
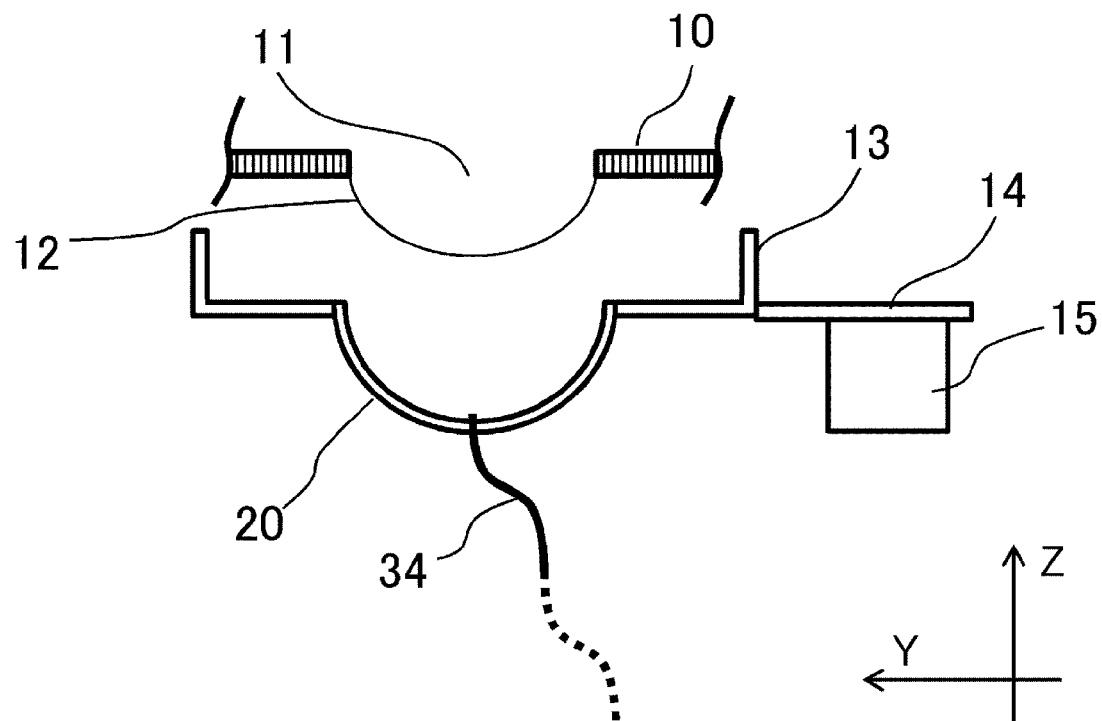

FIG. 11B is a diagram showing the structure of the portion of the photoacoustic imaging apparatus of the first embodiment of the present invention for observing the breast, and is a schematic diagram of the A-B cross section of FIG. 11A. In FIG. 11B, the horizontal direction of the diagram is the Y axis, the vertical direction of the diagram is the Z axis, and the perpendicular direction of the diagram (depth direction of the paper surface) is the X axis.

In FIG. 11B, reference numeral 20 is a detector, and is structured so that the receiving surfaces of at least certain ultrasound transducers among a plurality of ultrasound transducers which receive acoustic waves from an object are provided at respectively different angles. A more favorable mode is a detector having a configuration of being provided in a spherical shape so that the directivity of the plurality of ultrasound transducers faces the center of the sphere. To put it differently, the direction in which the reception sensitivity of each ultrasound transducer (CMUT probe) is highest is preferably facing the object but mutually different.

In order to perform favorable image reconstruction with a photoacoustic imaging apparatus, the ultrasound transducers are preferably disposed in a spherical shape so that the direction of the reception sensitivity of a plurality of ultrasound transducers faces the center of the sphere. This is in order to increase the sensitivity of the object portion in light of the fact that the directivity of the ultrasound transducers is limited. Moreover, this configuration is able to improve the image quality of the reconstructed image since the ultrasound transducers can be arranged to forma large solid angle relative to the object. In other words, the ultrasound transducers of the detector 20 are suitably arranged in a spherical shape so as to surround the object in order to achieve high quality image reconstruction.

Note that, typically, the normal direction of the receiving face (surface) of the conversion element becomes the direction in which the reception sensitivity is the highest. Thus, by arranging the ultrasound transducers along the spherical surface, the direction in which the reception sensitivity of each conversion element is higher than a predetermined level can be caused to face an area (specified region) that is near the center of a semispherical curvature. It can be said that this kind of arrangement is an arrangement in which the directional axis (axis along the direction in which the reception sensitivity is the highest) of at least certain conversion elements among a plurality of conversion elements is bundled. Specifically, the preferred arrangement is such that the direction in which each reception sensitivity of at least certain conversion elements among a plurality of conversion elements intersects with each other.

Moreover, it can be said that this kind of arrangement is an arrangement such that the receiving surfaces of the conversion elements face the inner side of the detector. In other words, when the conversion elements are provided to a support comprising a curved surface such as a spherical surface, the receiving surfaces of the conversion elements are disposed along the surface on the center side of the curvature. When the conversion elements are provided to a support comprising a surface configured from a combination of a plurality of flat surfaces (angle formed by the respective flat surface is preferably an obtuse angle), the receiving surfaces are arranged along the inner surface thereof (surface on the concave side).

As a result of adopting the foregoing configuration, the region in which the reception sensitivity of the respective conversion element is facing a direction that is higher than a predetermined level can attain higher resolution. In the present specification the region that can undergo reception at a high sensitivity is referred to as a high sensitivity region, and the high sensitivity region consequently becomes a high resolution region. Note that a preferred range of the high resolution region is a region from the point of the highest resolution to a range that becomes half the resolution of the highest resolution. The high sensitivity region that is determined based on the arrangement of a plurality of conversion elements is formed in a region where the object is assumed to be disposed during the inspection.

However, in the respective embodiments of the present invention, the arrangement of the plurality of conversion elements is not limited to the foregoing example. Preferably, the arrangement enables the high sensitivity reception of acoustic waves compared with the arrangement where the direction in which the reception sensitivity of each conversion element is highest is parallel to each other.

Note that, in the present specification, a "spherical surface" includes a spherical surface other than the surface of a true spherical shape. In other words, a "spherical surface" includes a spherical surface having an opening such as a semispherical surface. Moreover, a "spherical surface" also includes a surface having an unevenness on a surface that can be deemed a spherical surface, and a surface of an oval shape that can be deemed a spherical surface (a shape in which an oval shape is expanded three-dimensionally, and a shape in which the surface is configured from a secondary curved surface).

Meanwhile, when giving consideration to the hardware cost and calculation amount of the reconstruction signal processing, the number of ultrasound transducers cannot be increased infinitely. For example, when a breast is the object, if the detector 20 is of a semispherical shape, a size having a radius of roughly 150 mm is required. For example, when 256 ultrasound transducers are mounted in the detector 20, one ultrasound transducer needs to be mounted per approximately 550 mm$^2$. In other words, the ultrasound transducers need to be mounted at a pitch of approximately 23 mm.

As described above, it is difficult to mount the CMUT element 210 and the current/voltage conversion circuit 211 by separating their distance, and they need to be arranged close to each other. Thus, when realizing ultrasound transducers with the CMUT elements 210 at sparse intervals as described above, the detector 20 is preferably realized by using a plurality of CMUT probes 21 in which the CMUT element 210 and the current/voltage conversion circuit 211 are mounted on one cabinet.

In FIG. 11B, reference numeral 10 is an examination table, reference numeral 11 is a detection window provided to the examination table 10, and reference numeral 12 is a breast holding member for holding the patient's breast. Reference numeral 13 is a detector table to which the detector 20 is mounted, reference numeral 14 is a support member which supports the detector table 13, reference numeral 15 is a detector scanning unit which moves the detector 20 to the intended position, and reference numeral 34 is an optical fiber which guides the laser beam. The detector scanning unit 15 is configured, for example, a stepping motor and an XYZ stage.

In addition, while not shown, the space between the detector 20 and the breast holding member 12, and the space between the breast holding member 12 and the breast (not shown) are filled with an impedance matching material. An impedance matching material is referred to as a matching layer, and matches the acoustic impedance of the respective spaces. As the impedance matching material, desirably used as a liquid having an acoustic impedance that is similar to the breast and the ultrasound transducer and which transmits pulsed light. Specifically, water, castor oil or gel is used.

By causing the portion of the breast observed with a photoacoustic imaging apparatus to have the foregoing structure, the image reconstruction of the breast (object) can be favorably performed.

First Embodiment

The first embodiment of the present invention is now explained in detail with reference to FIG. 1. FIG. 1 is a diagram showing the structure of the portion of the photoacoustic imaging apparatus of the first embodiment of the present invention for observing a breast. FIG. 1A is a schematic diagram viewing the detector of the photoacoustic imaging apparatus of the first embodiment of the present invention from the lower direction of the examination table 10. In FIG. 1A, the horizontal direction of the diagram is the X axis, the vertical direction of the diagram is the Y axis, and the perpendicular direction of the diagram (depth direction of the paper surface) is the Z axis.

In FIG. 1A, reference numeral 13 is a detector table, reference numeral 20 is a detector, and reference numeral 21 is a CMUT probe. The detector 20 has a configuration of being provided in a spherical shape so that the directivity (direction in which the reception sensitivity is highest) of the intended number of CMUT probes 21 faces the center of the sphere. FIG. 1A shows an example of 16 CMUT probes 21, but the number of CMUT probes is not limited thereto. In FIG. 1A, reference numerals 22a, 22b, 22c, 22d are relay boards, reference numeral 212 is a power distribution line, and reference numeral 213 is a signal wiring. Here, the detector 20 and the relay boards 22a, 22b, 22c, 22d are fixed to the detector table 13. In other words, the positional relation of the detector 20 and the relay boards 22a, 22b, 22c, 22d is fixed.

In FIG. 1A, for example, the CMUT probe 21 within the dotted line shown with "a" in the diagram is connected to the relay board 22a via the power distribution line 212 and the signal wiring 213. Moreover, the CMUT probe 21 within the dotted line shown with "b" is connected to the relay board 22b, the CMUT probe 21 within the dotted line shown with "c" is connected to the relay board 22c, and the CMUT probe 21 within the dotted line shown with "d" is connected to the relay board 22d via the power distribution line 212 and the signal wiring 213. Note that the power distribution line 212 and the signal wiring 213 extending from the CMUT probe 21 are shown for only one CMUT probe 21 in order to prevent the diagram from becoming complex in FIG. 1A. Needless to say, all 16 CMUT probes 21 are connected via the power distribution line 212 and the signal wiring 213. In addition, as described later, the power distribution lines in the relay board are bundled, and connected to an electrical power source described later with a number of power distribution lines that is fewer than the number of power distribution lines connected to the CMUT probe 21.

FIG. 1B is a schematic diagram of the C-D cross section of FIG. 1A. In FIG. 1B, the horizontal direction of the diagram is the X axis, the vertical direction of the diagram is the Z axis, and the perpendicular direction of the diagram (depth direction of the paper surface) is the Y axis. In FIG. 1B, reference numeral 13 is a detector table, reference numeral 20 is a detector, reference numeral 21 is a CMUT probe, reference numerals 22b, 22d are relay boards, reference numeral 34 is an optical fiber, reference numeral 212 is a power distribution line, and reference numeral 213 is a signal wiring. In FIG. 1B, the relay boards 22b, 22d are fixed to the detector table 13 with a mounting screw (not shown). In other words, the positional relation of the detector 20 and the relay boards 22b, 22c is fixed. Consequently, since the power distribution line 212 and the signal wiring 213 connecting the CMUT probe 21 and the relay boards 22b, 22c will not move, for example, they can be fixed to the detector 20 and the detector table 13, and the mounting region can thereby be reduced.

Figure 2:
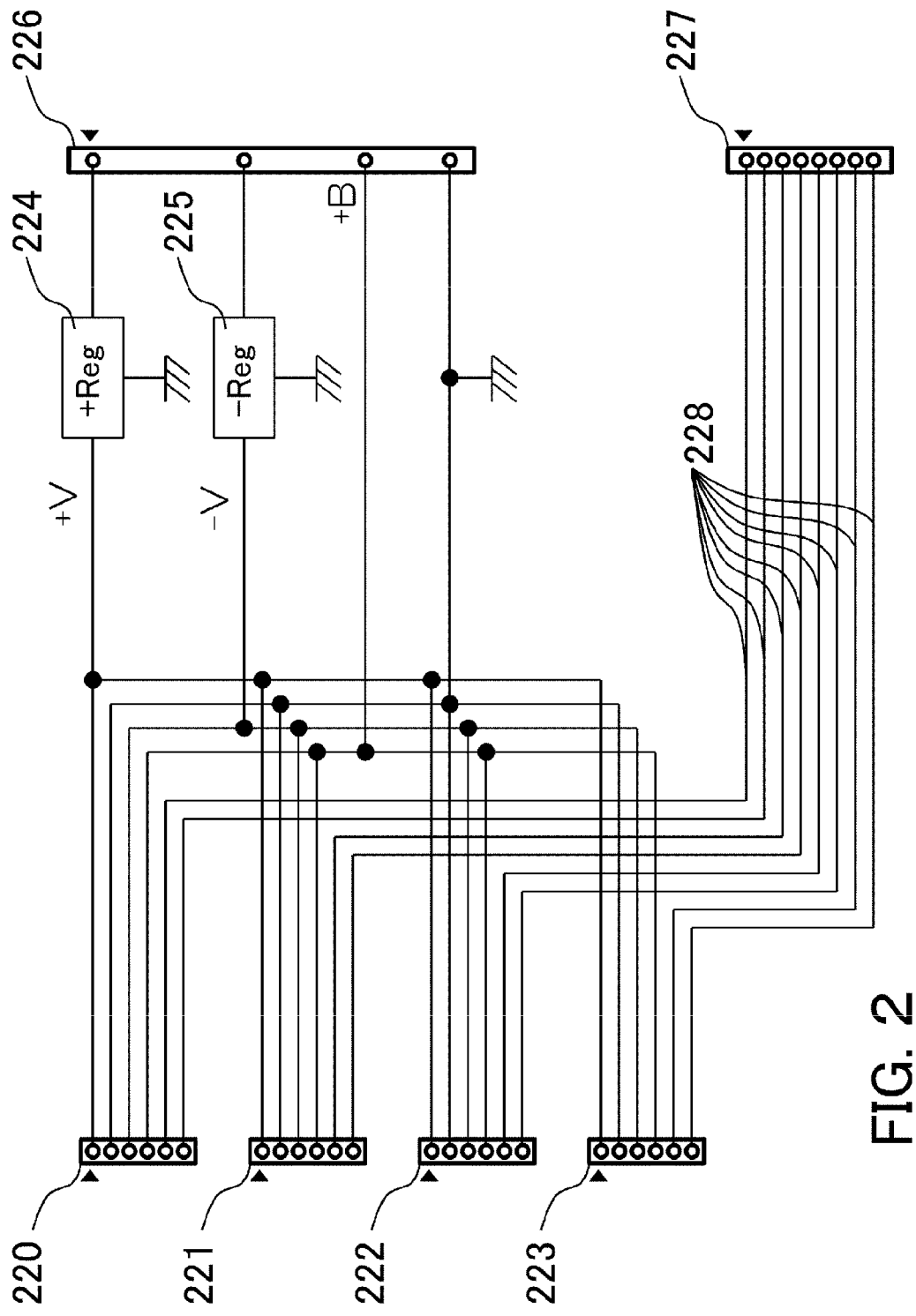
FIG. 2 is a circuit diagram of the relay board.

The relay boards 22a, 22b, 22c, 22d are now explained in detail. FIG. 2 shows a circuit diagram of the relay boards. The relay boards 22a, 22b, 22c, 22d are of the same circuit. In FIG. 2, reference numerals 220, 221, 222, 223 are connectors, reference numerals 224, 225 are local regulators, reference numeral 226 is a power source connector, reference numeral 227 is a signal connector, and reference numeral 228 is a signal wiring. The connectors 220, 221, 222, 223 to which the CMUT probe 21 is connected are each connected to the connector 214 (refer to FIG. 9A) of the CMUT probe 21.

This embodiment shows an example of four relay boards relative to 16 CMUT probes 21. In the foregoing case, the m-number (integer of 2 or more) of probes as the number of proves in the present invention is 16, and the n-number (integer of 2 or more; m≥n) of probes as the number of probes connected to one relay board is 4. Thus, the number of connectors 220, 221, 222, 223 to which the CMUT probe 21 is connected, which is connected per relay board, will be 4 connectors.

With the first embodiment of the present invention, explained was a case where four relay boards are used, and four CMUT probes 21 are connected to each relay board. Nevertheless, when the number of CMUT probes 21 and the number of relay boards are different, the number of connectors may be decided to match those numbers. For example, the configuration may also be such that the number of CMUT probes 21 connected to the relay board differs for each relay board. Moreover, the relay board may be shared and mounted so that the number of connections of the CMUT probe 21 will differ. Specifically, when there are ten CMUT probes 21, four relay boards having connectors to which four CMUT probes 21 are respectively connected may be prepared, and two, two, three and three CMUT probes 21 may be respectively connected to the relay boards. By sharing the relay board as described above, the design cost can be reduced since it is not necessary to create numerous types of relay boards.

Signals from the CMUT probe 21 are connected to the signal connector 227 via the signal wiring 228. Here, the wiring pattern is designed so that no noise will get mixed in. Moreover, the signal wirings are not particularly bundled. Meanwhile, the power distribution lines of the CMUT probe 21 correspond to the first to fourth pins of the connectors 220, 221, 222, 223. These power distribution lines are bundled and connected to the power source connector 226. In the first embodiment of the present invention, there are four CMUT probes 21 and there are four power distribution lines for each CMUT probe 21, so a total of 16 wirings are bundled as 4 wirings. The CMUT probe 21 and the relay boards 22a, 22b, 22c, 22d need to be connected via the power distribution line 212 and the signal wiring 213 with numerous wirings. Thus, the relay boards 22a, 22b, 22c, 22d are arranged around the detector 20. In addition, the length of the power source connector 226 of the relay board and the length of the wiring from the signal connector 227 to the electrical power source described later will become relatively long. By arranging the relay boards as described above, the effect of reducing the number of power distribution lines can be further exhibited.

Meanwhile, the following problems may arise with this kind of mounting. In other words, a voltage drop of the wiring may occur between the power source connector 226 as a bundle of the power distribution lines of the CMUT probe 21, and the electrical power source described later.

This is caused by the increase of current caused by the bundling of the power distribution lines of the CMUT probe 21, and the increase in the electrical resistance due to the long length of the wiring from the power source connector 226 to the electrical power source described later. Thus, as shown in FIG. 2, the voltage is stabilized and supplied to the CMUT probe 21 by adding local regulators 224, 225 between the wirings that send power to the CMUT probe 21. The local regulators may be an integrated circuit or the like referred to as a three-terminal regulator IC, or the stabilized power source circuit may be configured from discreet parts. Moreover, since hardly any current flows to the bias power source of the three pins of the power source connector 226, the voltage drop explained above will hardly occur. Thus, there is no problem even if local regulators are not mounted.

Moreover, in order to attenuate the noise that got mixed in due to the long length of the wiring from the power source connector 226 to the electrical power source described later, it would be more preferable to add a noise filter (not shown) to the power source line of the relay board in order to reduce the power source noise. A noise filter is realized with a filter based on the inductance component of ferrite beads and the capacitance of the capacitor, a filter based on a resistor and a capacitor, or a combination thereof.

As described above, wirings are connected to the relay boards via a connector. If the wiring of the CMUT probe 21 and the relay board is connected using a connector at least at one or more locations, the CMUT probe 21 can be replaced easily. More preferably, a connector is mounted on the rear face of the CMUT probe 21 so that the CMUT probe 21 and the wiring can be completely separated. By adopting the foregoing configuration, since the maintenance operation can be performed in a manner in which the position of the power distribution line 212 and the signal wiring 213 between the CMUT probe 21 and the relay board is fixed, the CMUT probe 21 can be replaced even more easily. This advantage becomes more significant in the case of a detector 20 with numerous wirings and which is mounted with numerous CMUT probes 21.

Figure 3:
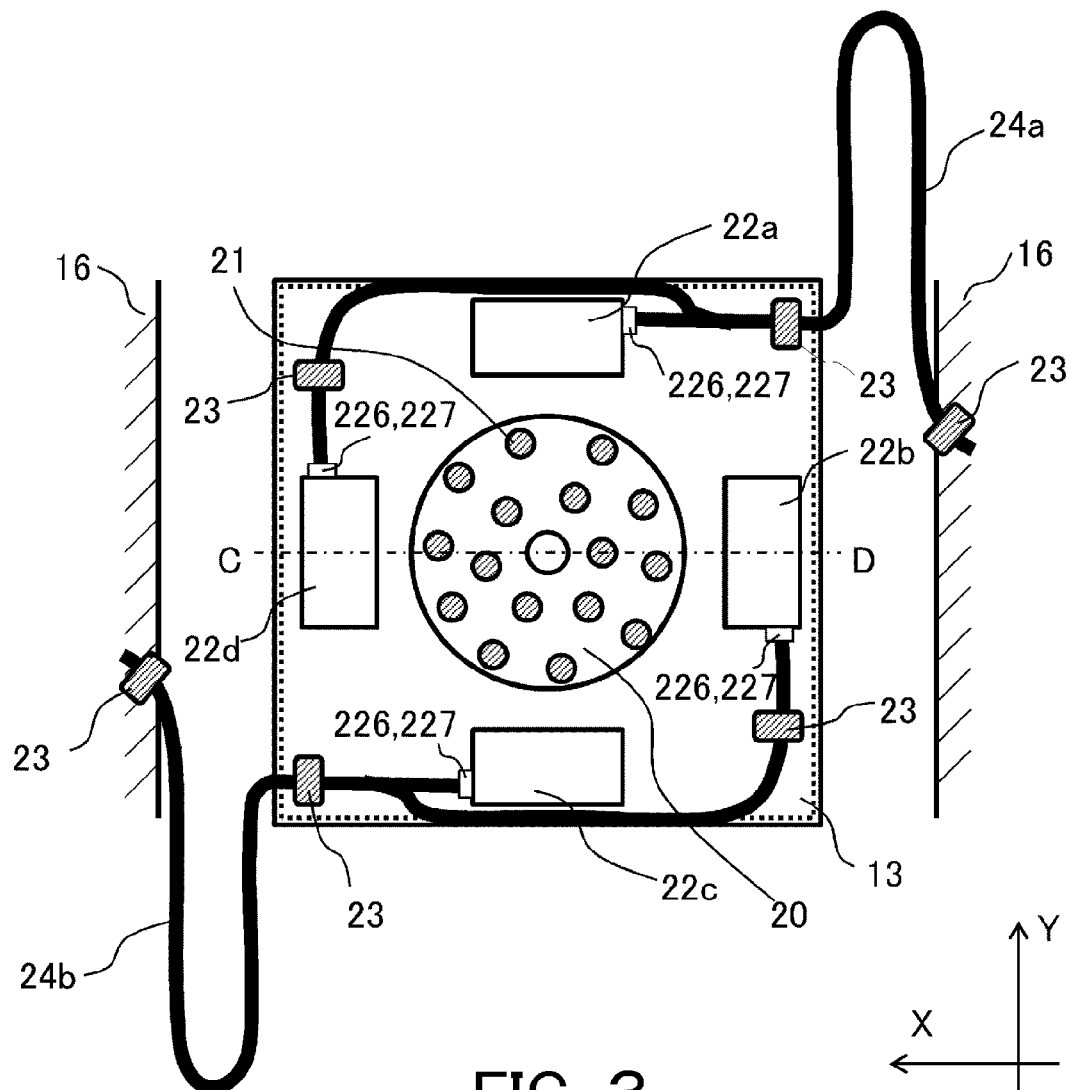
FIG. 3 is a schematic diagram of the detector of the photoacoustic imaging apparatus of the first embodiment.

The mounting method of the wirings from the relay boards is now explained. FIG. 3 is also a schematic diagram, as with FIG. 1A, viewing the detector of the photoacoustic imaging apparatus of the first embodiment from the lower direction of the examination table 10. In FIG. 3, the horizontal direction of the diagram is the X axis, the vertical direction of the diagram is the Y axis, and the perpendicular direction of the diagram (depth direction of the paper surface) is the Z axis. FIG. 3 is a schematic diagram for facilitating the understanding of the wirings to be connected to the relay boards. In FIG. 3, explanation of previously explained reference numerals is omitted.

In FIG. 3, reference numeral 16 is a frame that is fixed to the examination table 10, and reference numeral 23 is a wiring fixing member. Reference numeral 24a is a cable that bundles the wirings from the power source connector 226 and the signal connector 227 of the relay board 22a and the relay board 22d, respectively. Reference numeral 24b is a cable that bundles the wirings from the power source connector 226 and the signal connector 227 of the relay board 22b and the relay board 22c, respectively. Moreover, while the power distribution line 212 and the signal wiring 213 are located between the respective CMUT probes 21 and the relay boards 22a, 22b, 22c, 22d, the illustration thereof has been omitted to prevent the diagram from becoming complicated. In FIG. 3, the wirings from the power source connector 226 and the signal connector 227 have been bundled, but they may also be cables of separated configurations as a matter of course. For the wirings from the power source connector, a highly pressure-resistant cable is required since a bias voltage is included. By separating the wirings from the signal connector 227, there is an advantage in that a low pressure-resistant (that is, thin) cable can be used.

The cable 24a and the cable 24b are fixed to the detector table 13 and the frame 16 with a fixing member 23. The detector 20 and the detector table 13 scan (move) relative to the breast holding member 12 which is fixed to the examination table 10. In other words, the detector table 13 moves relative to the frame 16. Here, the movable portions of the cables 24a, 24b are preferably mounted in the guide of a flexible cable referred to as the cable bear (registered trademark). Since the specific method of scanning (moving) relative to the breast holding member 12 is described in detail in US Patent Application Publication No. 2011/0306865 and Japanese Patent Application Laid-open No. 2012-179348, the detailed explanation thereof is omitted. Since the number of wires of the cable 24a and the cable 24b as the movable portions can be reduced according to the mounting described above, the actuator of the detector scanning unit 15 that scans (moves) the detector table 13 can be a type having a small output.

Figure 4:
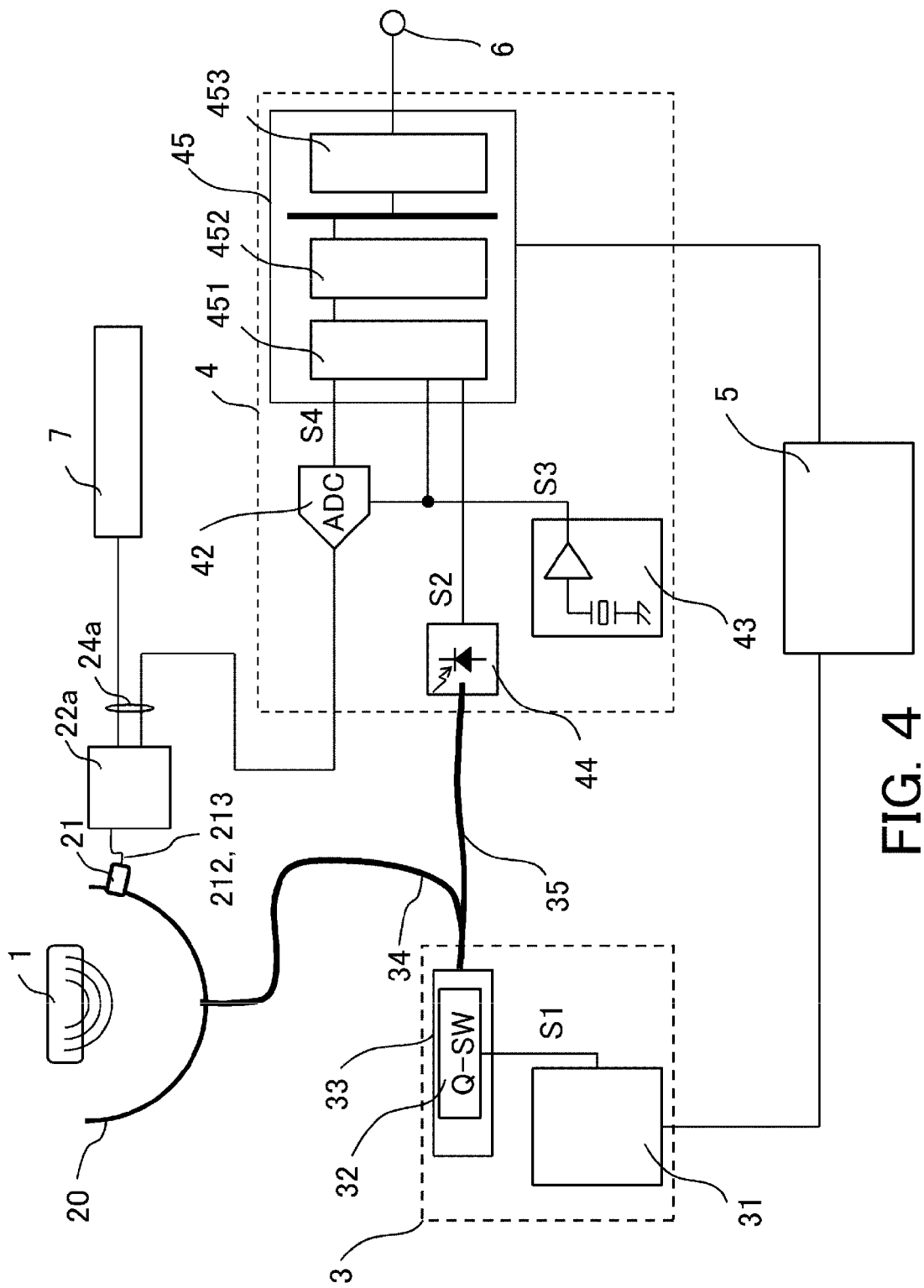
FIG. 4 is an electric circuit block diagram of the photoacoustic imaging apparatus.

The circuit configuration and operation of the photoacoustic imaging apparatus of the first embodiment are now explained with reference to the electric circuit block diagram of FIG. 4. In FIG. 4, reference numeral 1 denotes an object—a breast, reference numeral 3 denotes a laser pulse transmission unit, reference numeral 4 denotes a receiver, reference numeral 5 denotes a system control unit, reference numeral 6 denotes an output terminal of image data, and reference numeral 7 denotes an electrical power source which supplies power to the CMUT probe 21.

In the laser pulse transmission unit 3, reference numeral 31 is a laser emission control circuit, reference numeral 32 is a Q switch, and reference numeral 33 is a laser device.

Near the object 1, reference numeral 20 is a detector, reference numeral 21 is a CMUT probe, reference numeral 22a is a relay board, and reference numeral 24a is a cable. Only one CMUT probe 21 is shown and only the corresponding relay board 22a and wirings are shown to prevent the diagram from becoming complicated, but the other CMUT elements also have the same configuration. Reference numeral 34 is an optical fiber which guides a laser beam to the detector 20, and reference numeral 35 is an optical fiber which conveys the laser emission time to the receiver 4.

In the receiver 4, reference numeral 42 is an AD converter. Reference numeral 43 is a reception reference clock circuit and supplies a sampling clock of the AD converter 42. Reference numeral 44 is an optical detectors which converts a laser pulse guided by the optical fiber 35 into an electric signal. Reference numeral 45 is a signal processing unit which performs signal processing to digital data (photoacoustic data) converted with the AD converter 42. Reference numeral 451 is a write control circuit, reference numeral 452 is a memory of FIFO or the like, and reference numeral 453 is a signal processing circuit. As described above, in the diagram, only one among the plurality of CMUT probes 21 provided to the detector 20 is shown, and the receiver 4 actually comprises memories 452 in parallel for each of the plurality of CMUT elements.

In the configuration of FIG. 4, the laser emission control circuit 31 outputs an oscillation starting signal S1 to a Q switch 32 according to the laser emission instruction from the system control unit 5 as the light irradiation timing control means. The laser device 33 applies a laser pulse at the timing of the oscillation starting signal S1. Here, the Q switch 32 may also be an oscillation control means of a different configuration. For example, in the case of a semiconductor laser, since a sufficiently fast response is possible with direct modulation, a modulation driver may be used without using a Q switch. In other words, the modulation driver becomes the oscillation control means. The laser pulse is guided by the fiber 34 and applied to the object 1.

The laser pulse that entered the object 1 generates photoacoustic waves according to the absorption efficiency of the object 1. The receiver 4 receives the photoacoustic waves as described below, perform image reconstruction, and thereby generates image data of a tomographic image. The photoacoustic waves input to the CMUT element are converted into an analog electric signal (photoacoustic signal) and then output. The converted analog electric signal (photoacoustic signal) is converted into digital data (photoacoustic data) S4 with the AD converter 42. Moreover, signal amplification processing is executed as needed.

Meanwhile, the sampling clock S3 input to the AD converter 42 is a stable reference clock with minimal jitters that was created with the reception reference clock circuit 43. The timing of writing into the memory 452 of the photoacoustic data S4 is determined based on the light-receiving trigger signal S2 as the output of the optical detector 44. In addition, an intended number of AD-converted digital data (photoacoustic data) S4 on and after the determined write timing is sequentially stored in the memory 452. In other words, the write control circuit 451 consecutively stores in the memory 452 the intended number of digital data (photoacoustic data) S4 that was AD-converted at the timing of the sampling clock S3 with the time that the light-receiving trigger signal S2 was input as the source.

The signal processing circuit 453 additionally reads the photoacoustic data corresponding to the other CMUT elements from the memory, performs signal processing (image reconstruction), and generates image data within the living body based on photoacoustic waves (tomographic imaging). Subsequently, the image data is output from the output terminal 6. While this embodiment specifically described the output terminal 6 which outputs the reconstructed image data, for example, this may also be a network I/O terminal for storing the reconstructed image data in a memory (not shown) or a nonvolatile memory simply used for storage.

FIG. 4 explained a configuration of performing signal processing to the photoacoustic data with hardware, but this may also be software processing. In particular, image reconstruction is enabled in a relatively short period of time by using a multi-cored CPU. When processing is to be performed using software, read processing is performed from the memory 452. In the foregoing case, the irradiation timing of the laser pulse is desirably decided so that the load of the software processing is not concentrated. Various know methods such as phasing may be used for the image reconstruction.

Power to the CMUT probe 21 is supplied from the electrical power source 7. For example, the electrical power source 7 is disposed within the same rack as the receiver 4. When the local regulators are mounted with the relay boards 22a to 22d, the electrical power source 7 preferably outputs the voltage by giving consideration thereto. Specifically, output is a voltage that is greater than the I/O voltage drop of the local regulator, the voltage drop in the wirings from the respective relay boards to the electrical power source 7, and the voltage obtained by adding the power source voltage of the CMUT probe 21.

If the power source voltage of the electrical power source 7 is great, the design margin relative to the voltage drop of the wirings from the relay boards 22a to 22d to the electrical power source 7 can be increased, but the electric power consumption of the local regulators will increase, and result in the increased heating value. Thus, the electrical power source 7 should output a voltage value obtained by adding roughly 0.1 to 1 V to the voltage value of the minimum I/O voltage of the local regulators and the maximum voltage drop of the wirings from the relay boards 22a to 22d to the electrical power source 7. Note that a case of using a positive voltage regulator was explained, but in the case of a negative voltage regulator, this may be considered in terms of an absolute voltage. By setting the voltage of the electrical power source 7 as described above, the intended voltage can be stably applied to the CMUT probe 21.

According to the first embodiment, the number of wirings can be reduced by bundling the power distribution lines of the CMUT probe 21 with the relay boards 22a to 22d. Consequently, since the number of wirings of the cables 24a, 24b can be reduced, the mounting region of the cables 24a, 24b can also be reduced. In addition, an effect of being able to downsize the overall device is also yielded. Moreover, the number of wirings of the movable portion can be reduced by mounting the relay boards. In other words, thin cables can be used as the cables 24a, 24b. Consequently, the force applied in the case of scanning (moving) the detector 20 can be reduced. Consequently, since the size of the actuator for moving the detector table 13 can be reduced, an effect of reducing heat generation, reducing power consumption, and reducing costs is yielded.

As described above, the device of the first embodiment comprises a detector comprising an m-number (m is an integer of 2 or more) of probes including a capacitance conversion element and a current/voltage conversion circuit, a receiver which processes signals derived from acoustic waves from the object, and a relay board which connects the electrical power source and the probes. The relay boards connect the electrical power source and the probes and the receiver and the probes via power distribution lines and signal wirings, respectively. In addition, the relay boards receive input of n-number (n is an integer of 2 or more; m≥n) of signal wirings and power distribution lines, and connect the signal wirings from the n-number of probes to the receiver without changing the number of signal wirings (same number), and connect the power distribution lines in a number that is fewer than the power distribution lines from the n-number of probes to the electrical power source side.

Based on this kind of configuration, it is possible to reduce the cable mounting region, and an effect of downsizing the overall device is yielded. Moreover, in the case of comprising a scanning unit for moving the detector, a thin cable can be used as the cable of the movable part by fixing the positional relation of the detector and one or more relay boards. Consequently, a small actuator can be used for moving the detector table 13, and an effect of reducing heat generation, reducing power consumption, and reducing costs is yielded.

Second Embodiment

Figure 5:
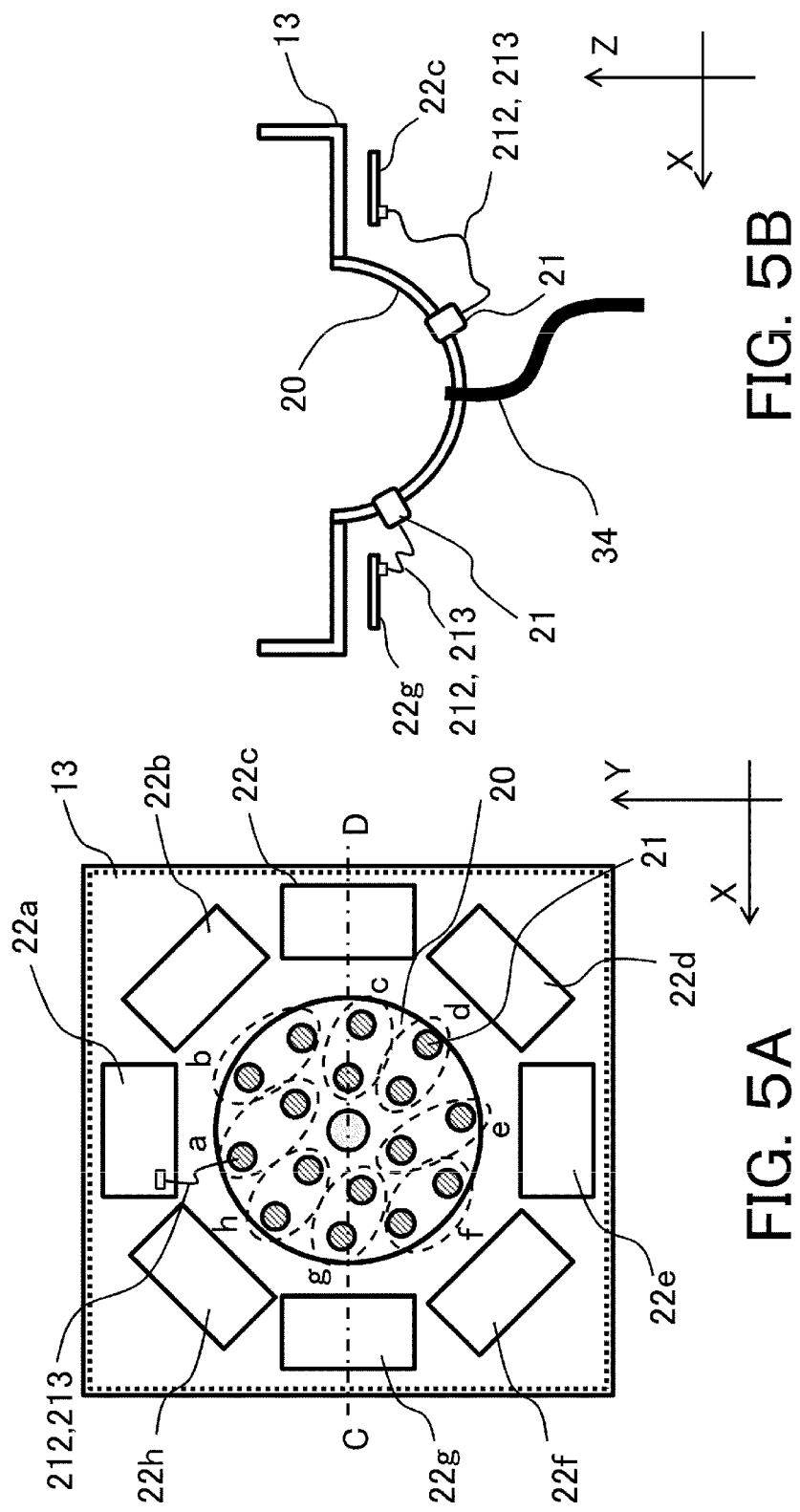
FIGS. 5A and 5B are diagrams explaining the second embodiment.

The second embodiment to be explained with reference to FIG. 5 differs from the first embodiment with regard to the number of relay boards. FIG. 5A is a schematic diagram viewing the detector of the photoacoustic imaging apparatus of the second embodiment of the present invention from the lower direction of the examination table 10. In FIG. 5A, the horizontal direction of the diagram is the X axis, the vertical direction of the diagram is the Y axis, and the perpendicular direction of the diagram (depth direction of the paper surface) is the Z axis.

In FIG. 5A, reference numeral 13 is a detector table, reference numeral 20 is a detector, and reference numeral 21 is a CMUT probe. The detector 20 is of a semispherical shape, and comprises a plurality of CMUT probes 21 on a spherical surface. The directivity (direction in which the reception sensitivity is highest) of the respective CMUT probes 21 is arranged to face the center of the sphere. FIG. 5A shows an example of 16 CMUT probes 21, but the number of CMUT probes is not limited thereto. Moreover, the shape of the detector 20 is not limited to a semispherical shape, and it will suffice so as long as the directivity of at least certain CMUT probes can be arranged differently. For example, various detectors may be used; for instance, detectors of a bowl shape, a dish shape, or a shape in which a plurality of flat surfaces or curved surfaces are combined. Moreover, the term "semispherical shape" as used herein is not limited to an item having a plane that passes through the exact center of the sphere as its cross section. In the foregoing case, the shape of the container will be smaller (or larger) than a strict semispherical shape.

In FIG. 5A, 22a, 22b, 22c, 22d, 22e, 22f, 22g, 22h are relay boards, 212 is a power distribution line, and 213 is a signal wiring. Here, the detector 20 and the relay boards 22a to 22h are fixed to the detector table 13. In other words, the positional relation of the detector 20 and the respective relay boards 22a to 22h is fixed. In FIG. 5A, the two CMUT probes 21 within the dotted line "a" are connected to the relay board 22a via the power distribution line 212 and the signal wiring 213. Moreover, the CMUT probe 21 within the dotted line "b" is connected to the relay board 22b, the CMUT probe 21 within the dotted line "c" is connected to the relay board 22c, the CMUT probe 21 within the dotted line "d" is connected to the relay board 22d, and the CMUT probe 21 within the dotted line "e" is connected to the relay board 22e. Moreover, the CMUT probe 21 within the dotted line "f" is connected to the relay board 22f, the CMUT probe 21 within the dotted line "g" is connected to the relay board 22g, and the CMUT probe 21 within the dotted line "h" is connected to the relay board 22h. Note that the power distribution line 212 and the signal wiring 213 extending from the CMUT probe 21 are shown for only one CMUT probe 21 in order to prevent the diagram from becoming complex. Nevertheless, in reality, all 16 CMUT probes 21 are connected to the power distribution line 212 and the signal wiring 213. In addition, as described above, the power distribution lines in the relay board are bundled, and connected to the electrical power source 7 described later with a number of power distribution lines that is fewer than the number of power distribution lines connected to the CMUT probe 21.

FIG. 5B is a schematic diagram of the C-D cross section of FIG. 5A. In FIG. 5B, the horizontal direction of the diagram is the X axis, the vertical direction of the diagram is the Z axis, and the perpendicular direction of the diagram (depth direction of the paper surface) is the Y axis. In FIG. 5B, reference numeral 13 denotes a detector table, reference numeral 20 denotes a detector, reference numeral 21 denotes a CMUT probe, reference numerals 22c, 22g denote relay boards, reference numeral 34 denotes an optical fiber, reference numeral 212 denotes a power distribution line, and reference numeral 213 denotes a signal wiring. In FIG. 5B, the relay boards 22c, 22g are fixed to the detector table 13 with a mounting screw (not shown). In other words, the positional relation of the detector 20 and the relay boards 22c, 22g is fixed. Consequently, since the power distribution line 212 and the signal wiring 213 connecting the CMUT probe 21 and the relay boards 22c, 22g will not move, for example, they can be fixed to the detector 20 and the detector table 13, and the mounting region can thereby be reduced.

Since the relay boards 22a to 22h in the second embodiment only differ from the first embodiment with regard to the number of CMUT probes 21 that are connected, the detailed explanation thereof is omitted.

In the second embodiment, shown is a configuration of receiving inputs from two CMUT probes 21 with the relay boards for the sake of explanation. More preferably, relay boards for receiving the input from 8 to 128 CMUT probes 21 may be used. As a specific example, the number of CMUT probes 21 to be mounted on the detector 20 shall be 512 and the number of relay boards shall be 8. In the foregoing case, 64 CMUT probes 21 are input for each relay board. As another example, the number of CMUT probes 21 to be mounted on the detector 20 shall be 32 and the number of relay boards shall be one. In the foregoing case, all 32 CMUT probes 21 are input for each relay board. The number of relay boards may be determined from the foregoing conditions and the mountable region of the device. Moreover, when the number of relay boards is great, numerous mechanisms for mounting the relay boards become required, and the mechanism becomes complex and the cost will increase. Thus, the number of relay boards shall be 16 or less.

Moreover, when there are multiple relay boards, as shown in FIG. 1A and FIG. 5A, the relay boards are preferably arranged substantially concentrically around the detector 20. By adopting this kind of arrangement, since the wirings between the relay boards and the CMUT probes can be shared, an effect of reducing the types of wirings can be yielded.

With regard to the mounting method of the wirings from the relay boards to the electrical power source 7 and the receiver 4, the wirings from the power source connector 226 and the signal connector 227 of one or more relay boards are bundled as a cable. For example, similar to the first embodiment, the wirings from the power source connector 226 and the signal connector 227 of two relay boards are bundled into four cables. As described above, the wirings from the power source connector 226 and the signal connector 227 may also be separately bundled and mounted. Moreover, in the case of scanning (moving) the detector 20 (detector table 13) also, as with the first embodiment, the cables are preferably fixed to the detector table 13 and the frame 16, and mounted in the guide of a flexible cable referred to as the cable bear (registered trademark).

Since the remaining configuration is the same as the first embodiment, the explanation thereof is omitted.

The foregoing description explained a case of physically mounting 8 relay boards. As another mode of the second embodiment, the physical number of relay boards is the same as the first embodiment at 4 relay boards, but may also be 8 relay boards in terms of an electric circuit. In other words, this is a configuration where the relay boards 22a to 22d of FIG. 1 each have two independent electric circuits. In this kind of mode, since the physical number of relay boards is small, the mounting mechanism can be simplified. Moreover, similar to the case of physically mounting 8 relay boards, there is also an advantage in that the current flowing through the power distribution lines of the relay board 22 and the electrical power source 7 can be distributed and the voltage drop can be reduced, and the power consumption per local regulator can be reduced, and the radiator can be simplified.

According to the second embodiment, as with the first embodiment, the number of wirings can be reduced by bundling the power distribution lines of the CMUT probe 21 with the relay boards 22a to 22h. Consequently, since the number of wirings of the cables from the relay boards 22a to 22h can be reduced, the mounting region can also be reduced. In addition, an effect of being able to downsize the overall device is also yielded. Moreover, upon scanning (moving) the detector 20, the number of wirings of the movable portion can be reduced by mounting the relay boards. Consequently, the movable portions can be moved with less force. In other words, since the size of the actuator for moving the detector table 13 can be reduced, an effect of reducing heat generation, reducing power consumption, and reducing costs is yielded.

In addition, according to the second embodiment of the present invention, by determining the number of relay boards based on the number of CMUT probes 21 to be mounted on the detector 20, mounting that is compatible with the mountable region of the device becomes possible. Moreover, by causing the number of relay boards to be 1 or more and 16 or less, a cost reduction effect is yielded. In addition, when there are multiple relay boards, by arranging the relay boards substantially concentrically around the detector 20, the wirings between the relay boards and the CMUT probe 21 can be shared, and a cost reduction effect is yielded upon production.

As explained above, with the device of the second embodiment, the number of relay boards is 1 or more and 16 or less, and arranged substantially concentrically around the detector 20. By adopting this kind of configuration, an effect of reducing costs and reducing the types of wirings between the CMUT probes 21 can be yielded.

Third Embodiment

In the third embodiment, the shape of the relay boards is considerably different from the first and second embodiments. In the third embodiment, by devising the shape of the relay boards, the length of the wirings of the CMUT probe 21 and the relay board can be further shortened, and the power distribution lines and signal wiring can also be shared.

The third embodiment is now explained in detail with reference to FIG. 6. FIG. 6A is a schematic diagram viewing the detector of the photoacoustic imaging apparatus of the third embodiment of the present invention from the lower direction of the examination table 10. In FIG. 6A, the horizontal direction of the diagram is the X axis, the vertical direction of the diagram is the Y axis, and the perpendicular direction of the diagram (depth direction of the paper surface) is the Z axis.

In FIG. 6A, reference numeral 13 is a detector table, reference numeral 20 is a detector, and reference numeral 21 is a CMUT probe. The detector 20 is of a semispherical shape, and comprises a plurality of CMUT probes 21 on a spherical surface. The directivity (direction in which greater reception sensitivity is exhibited) of the respective CMUT probes 21 is arranged to face the center of the sphere. FIG. 6A shows an example of 16 CMUT probes 21, but the number of CMUT probes is not limited thereto. Moreover, the shape of the detector 20 is not limited to a semispherical shape, and it will suffice so as long as the directivity of at least certain CMUT probes can be arranged differently.

Figure 6:
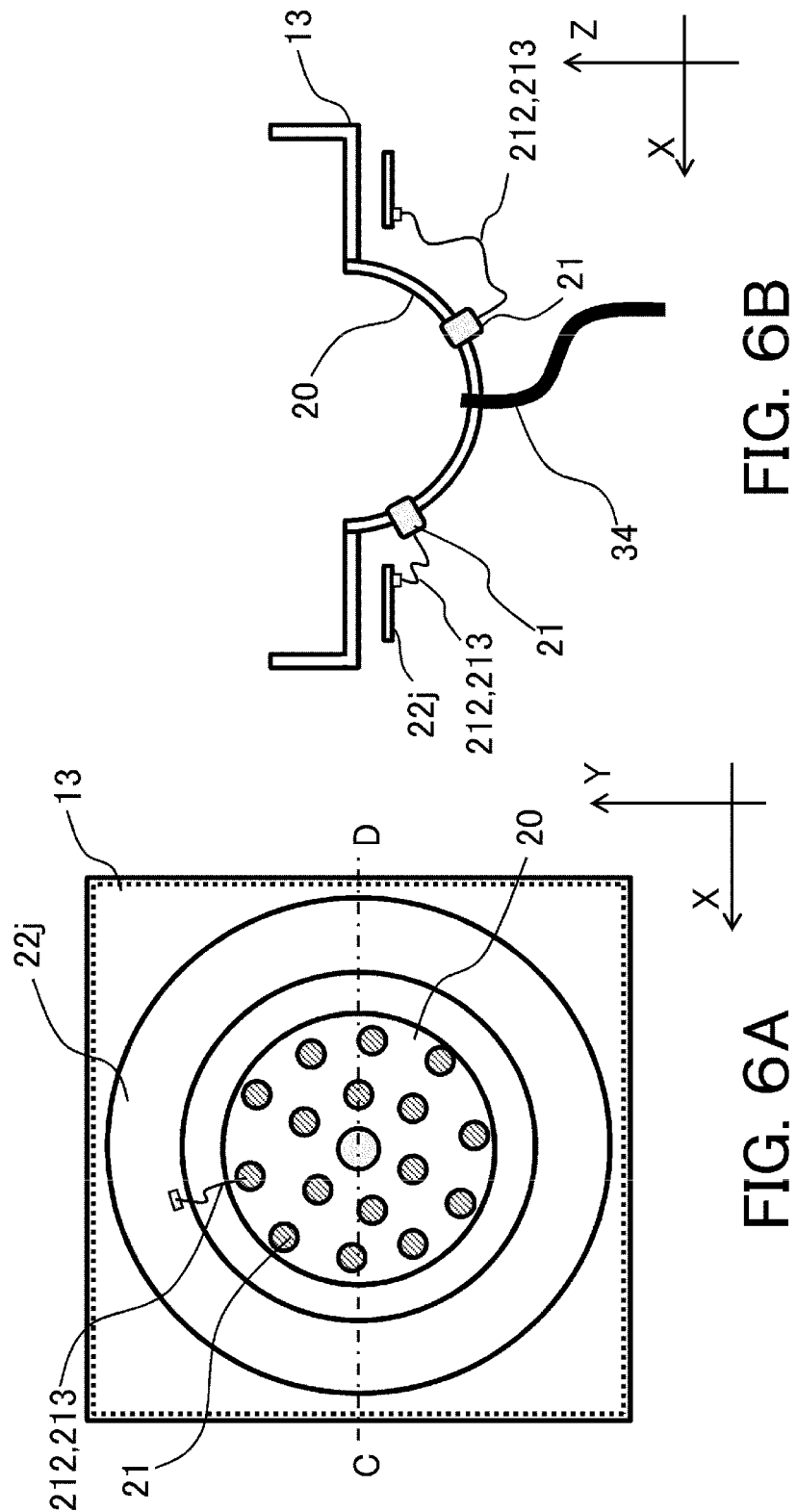
FIGS. 6A and 6B are diagrams explaining the third embodiment.

In FIG. 6A, 22j is a relay board. The shape of the relay board 22j is a doughnut-like disk shape that is substantially concentric with the detector 20 as evident from the diagram. In the case of FIG. 6, m-number of probes as the number of probes in the present invention is 16, and n-number of probes as the number of probes to input wirings in one relay board is also 16 (among cases where m≥n, case where m=n).

FIG. 6B is a schematic diagram of the C-D cross section of FIG. 6A. In FIG. 6B, the horizontal direction of the diagram is the X axis, the vertical direction of the diagram is the Z axis, and the perpendicular direction of the diagram (depth direction of the paper surface) is the Y axis. In FIG. 6B, reference numeral 13 is a detector table, reference numeral 20 is a detector, reference numeral 21 is a CMUT probe, reference numeral 22j is a relay board, reference numeral 34 is an optical fiber, reference numeral 212 is a power distribution line, and reference numeral 213 is a signal wiring.

In FIG. 6B, the relay board 22j is fixed to the detector table 13 with a mounting screw (not shown). The relay board 22j is mounted so that the center position of the detector and the center position of the relay board 22j are substantially the same. In other words, the positional relation of the detector 20 and the relay board 22j is fixed. Consequently, since the power distribution line 212 and the signal wiring 213 connecting the CMUT probe 21 and the relay board 22j will not move, for example, they can be fixed to the detector 20 and the detector table 13, and the mounting region can thereby be reduced.

In FIG. 6A, the CMUT probe 21 is connected to the relay board 22j via the power distribution line 212 and the signal wiring 213. Unlike the first embodiment and the second embodiment, since the shape of the relay board 22j is of a doughnut-like disk shape (donut shape), upon arranging the connector on the relay board 22j, the arrangement can be such that the distance between the CMUT probe 21 and the connector becomes minimum. Consequently, the length of the power distribution line 212 and the signal wiring 213 for connecting the CMUT probe 21 and the relay board 22j can be shortened. Note that the illustration of the power distribution line 212 and the signal wiring 213 has been omitted in FIG. 6A to prevent the diagram from becoming complicated. Nevertheless, in reality, all 16 CMUT probes 21 are connected to the power distribution line 212 and the signal wiring 213. In addition, as described above, the power distribution lines in the relay board are bundled within the relay board 22j, and connected to the electrical power source 7 with a number of power distribution lines that is fewer than the number of power distribution lines connected to the CMUT probe 21.

Since the number of relay boards is one relay board in the third embodiment, when the number of CMUT probes 21 to be mounted on the detector 20 is great, as illustrated in the second embodiment, a configuration of a plurality of electric circuits should be arranged in one physical printed circuit board. For example, in one doughnut-like disk shape relay board 22j, four independent circuits are designed to be configured as electric circuits. Consequently, since the current flowing through the power distribution lines of the relay board 22j and the electrical power source 7 can be distributed, the voltage drop can be reduced. Moreover, since the regulator IC can be divided in relation to the heat generation of local regulators, the respective radiators can be downsized. The number of divisions in terms of electric circuits is not limited to four, and may be set in accordance with the various conditions of the device. For example, the number of divisions may be suitable set to 1 to 16.

In addition, with the third embodiment, compared with the first and second embodiments, by causing the relay board 22j to be one board having a doughnut-like disk shape, the mechanism for mounting the relay board 22j on the detector table 13 can be simplified.

Figure 7:
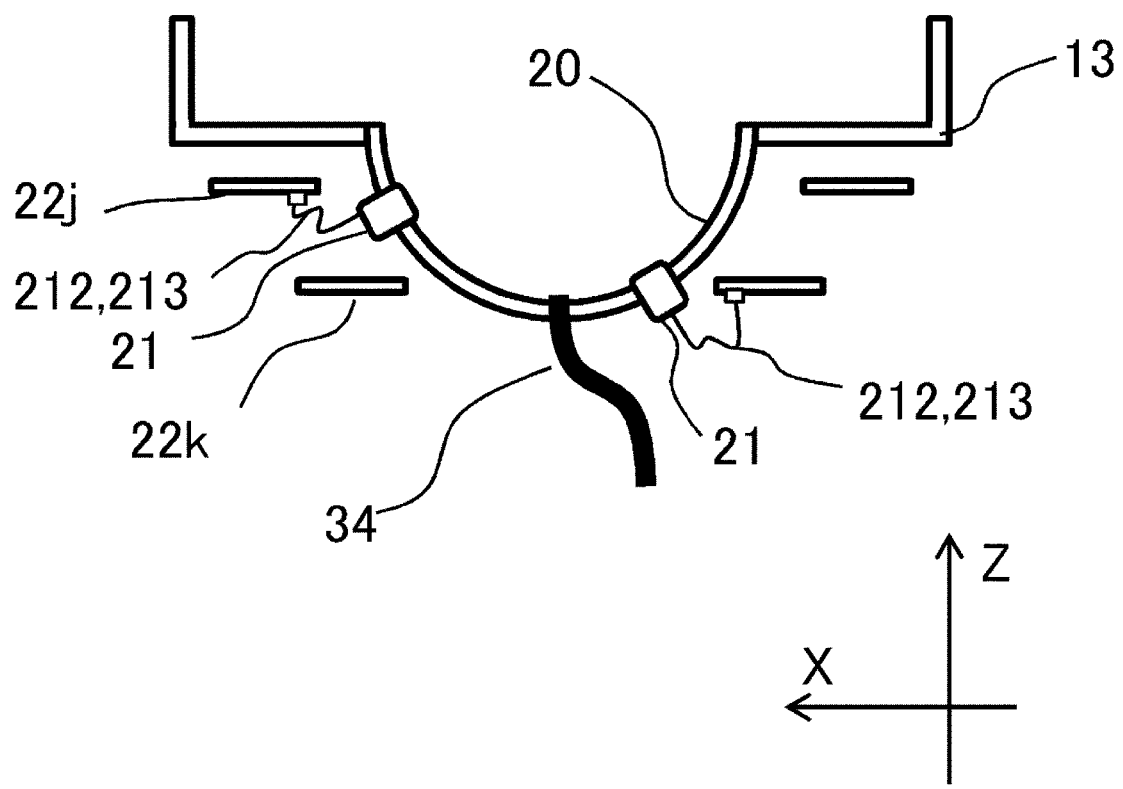
FIG. 7 is a diagram explaining another mode of the third embodiment.

A mounting example that differs from FIG. 6B of the third embodiment is shown in FIG. 7. In FIG. 7, the horizontal direction of the diagram is the X axis, the vertical direction of the diagram is the Z axis, and the perpendicular direction of the diagram (depth direction of the paper surface) is the Y axis. In FIG. 7, reference numeral 13 is a detector table, reference numeral 20 is a detector, reference numeral 21 is a CMUT probe, reference numerals 22j, 22k are relay boards, reference numeral 34 is an optical fiber, reference numeral 212 is a power distribution line, and reference numeral 213 is a signal wiring.

In FIG. 7, the relay boards 22j, 22k are each boards having a doughnut-like disk shape, and fixed to the detector table 13 with amounting screw (not shown). Here, the relay boards 22j, 22k are mounted so that the center position of the detector 20 and the center position of the relay boards 22j and 22k are substantially at the same location. Accordingly, the advantages of the mode of FIG. 6 can be enjoyed directly.

The major difference between the example of FIG. 7 and the configuration of FIG. 6 is in the point that there are two relay boards 22j, 22k of a doughnut-like disk shape having different diameters. As evident from FIG. 7, by using two relay boards 22j, 22k of a doughnut-like disk shape having different diameters, compared with the case of FIG. 6, the length of the power distribution line 212 and the signal wiring 213 for connecting the CMUT probe 21 and the relay board 22j can be further shortened. Consequently, the mounting region of the power distribution line 212 and the signal wiring 213 for connecting the CMUT probe 21 and the relay board 22 can be further reduced.

Since the relay boards 22j, 22k are merely shaped differently compared with the first embodiment and the second embodiment, the explanation of the remaining configuration is omitted.

According to the third embodiment, as with the first embodiment, the number of wirings can be reduced by bundling the power distribution lines of the CMUT probe 21 with the relay boards 22j, 22k. Consequently, since the number of wirings of the cables of the electrical power source 7 from the relay boards 22j, 22k can be reduced, the mounting region can also be reduced. In addition, an effect of being able to downsize the overall device is also yielded. Moreover, upon scanning (moving) the detector 20, the number of wirings of the movable portion can be reduced by mounting the relay boards. Consequently, the movable portions can be moved with less force. In other words, since the size of the actuator for moving the detector table 13 can be reduced, an effect of reducing heat generation, reducing power consumption, and reducing costs is yielded.

In addition, according to the third embodiment, the CMUT probe 21 to be mounted on the detector 20 and the relay boards 22j, 22k can be positioned close to each other. Thus, the mounting region of the CMUT probe 21 and the relay boards 22j, 22k can be reduced, and an effect of downsizing the device is yielded.

As explained above, with the device of the third embodiment, the shape of one or more relay boards is of a doughnut-like disk shape, and the center of the relay boards and the center of the container shape are of substantially the same position. Based on this kind of configuration, further downsizing of the device can be realized.

Fourth Embodiment

The fourth embodiment is a method of realizing the power distribution line 212 and the signal wiring 213 for connecting the CMUT probe 21 and the relay board of the first to third embodiments with a flexible printed circuit board.

In the case of this fourth embodiment also, similar to each of the foregoing embodiments, there is no change in the relative positional relation of the CMUT probe 21 and the relay board. In addition, since the power distribution line 212 supplies power to one CMUT probe 21, the demanded current value is small. Thus, the power distribution line 212 and the signal wiring 213 to be connected can be easily created with a flexible board.

When the power distribution line 212 and the signal wiring 213 are realized with a flexible board, compared with the case of using a cable, mounting is facilitated since there is no need for bundling. In particular, when the relay board is of a doughnut-like disk shape as in the third embodiment, since the wiring length of the power distribution line 212 and the signal wiring 213 can also be shortened, the cost increase that is of concern when realizing them with a flexible board can also be inhibited. Note that, also in the fifth embodiment described later, mounting is also facilitated by realizing the power distribution line 212 and the signal wiring 213 with a flexible printed circuit board.

Fifth Embodiment

The fifth embodiment is an embodiment that uses a flat detector as described in Japanese Patent Application Laid-open No. 2011-183057 unlike the semispherical or bowl-shaped detector explained in the first to fourth embodiments.

Figure 8:
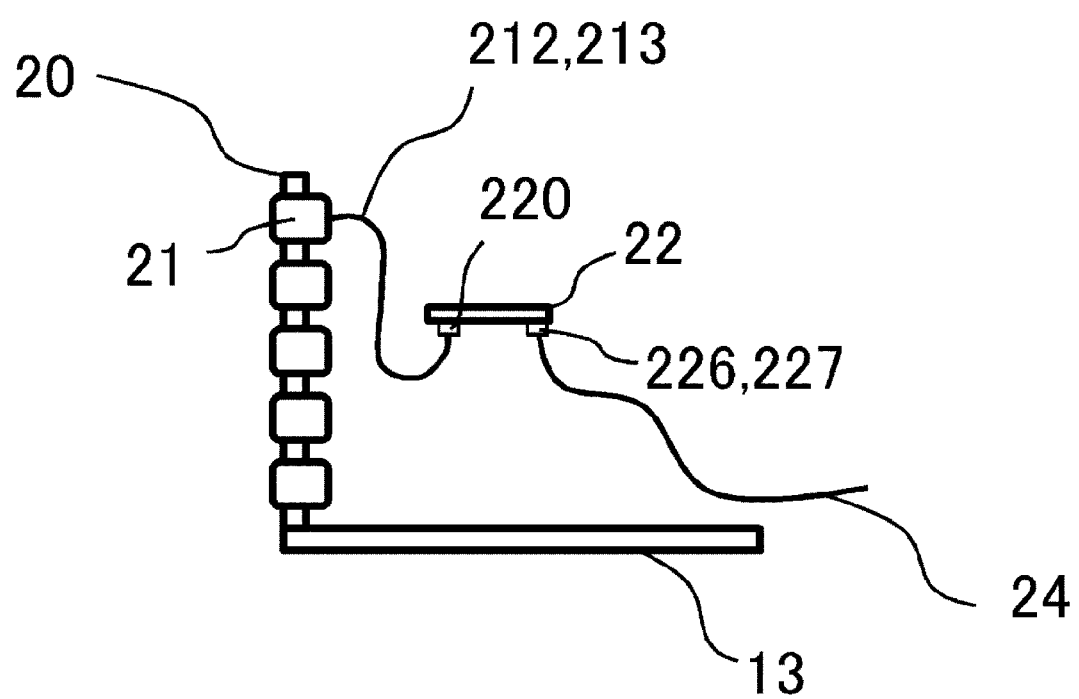
FIG. 8 is a diagram explaining the fifth embodiment.

In FIG. 8, reference numeral 13 is a detector table, reference numeral 20 is a detector, and reference numeral 21 is a CMUT probe. The planar detector 20 comprises a plurality of CMUT probes 21. The plurality of CMUT probes 21 are provided so that the directivity becomes parallel. In other words, the direction in which the sensitivity of the respective CMUT probes is high is substantially the same. The number of CMUT probes 21 is not limited to 5. The CMUT probes 21 are mounted in an intended number one-dimensionally or two-dimensionally.

In FIG. 8, reference numeral 22 is a relay board, reference numeral 220 is a connector, reference numeral 226 is a power source connector, reference numeral 227 is a signal connector, and reference numeral 24 is a cable of the power distribution line and the signal wiring. Here, the detector 20 and the relay board 22 are fixed to the detector table 13. In other words, the positional relation of the detector 20 and the relay board 22 is fixed. In FIG. 8, the CMUT probe 21 is connected to the connector 220 of the relay board 22 via the power distribution line 212 and the signal wiring 213. Note that the power distribution line 212 and the signal wiring 213 are illustrated only for one CMUT probe 21 to prevent the diagram from becoming complex in FIG. 8. Nevertheless, in reality, all 5 CMUT probes 21 are connected to the connector 220 via the power distribution line 212 and the signal wiring 213. And as described above, the power distribution lines are bundled within the relay board, and connected to the electrical power source 7 with the cable 24 using a number of power distribution lines that is fewer than the number of power distribution lines connected to the CMUT probe 21. As described above, the cable 24 may also be realized with two cables; namely, the cable of the power distribution line and the cable of the signal wiring.

Even when the detector 20 is of a flat shape as in this embodiment, the number of wirings can be reduced by bundling the power distribution lines of the CMUT probe 21 with the relay board 22. Consequently, since the number of wirings of the cable 24 is reduced, the mounting region of the cable 24 can also be reduced. Consequently, an effect of being able to downsize the overall device is also yielded. Moreover, upon scanning (moving) the detector 20, the number of wirings of the movable portion can be reduced by mounting the relay boards; that is, a thin cable can be used as the cable 24. Consequently, the movable portions can be moved with less force. In other words, since the size of the actuator for moving the detector table 13 can be reduced, an effect of reducing heat generation, reducing power consumption, and reducing costs is yielded.

As explained in each of the foregoing embodiments, according to the present invention, even when a CMUT probe is used as the ultrasound transducer of the detector, numerous power distribution lines can be bundled with the relay boards, and connection with the electrical power source can be realized with fewer power distribution lines. Thus, an effect of reducing the region that requires wirings from the CMUT probe is yielded. Consequently, the device can be downsized.

In addition, when moving the detector, by mounting the relay boards so that the positional relation of the detector and the relay boards is fixed and causing the wirings from the relay board to be movable parts, the mechanical resistance can be reduced. Consequently, an effect of downsizing the actuator as a moving means is also yielded.

While the present invention has been described with reference to exemplary embodiments, it is to be understood that the invention is not limited to the disclosed exemplary embodiments. For example, the present invention can be applied to a probe having a capacitance conversion element that executes signal processing in which small change of electrostatic capacity is treated as a change of voltage, even though all of the above described examples are explained by CMUT element. The scope of the following claims is to be accorded the broadest interpretation so as to encompass all such modifications and equivalent structures and functions.

This application claims the benefit of Japanese Patent Application No. 2014-056892, filed on Mar. 19, 2014, which is hereby incorporated by reference wherein in its entirety.

What is claimed is:

1. An object information acquiring apparatus comprising:
   a detector including m-number, where m is an integer of 2 or more, of probes having a capacitance conversion element to which a voltage is supplied from an electrical power source and a current/voltage conversion circuit which converts a current output from the capacitance conversion element into a voltage;
   a receiver processing electric signals from the probes; and
   a connecting relay board respectively relaying power distribution lines between the electrical power source and the probes and signal wirings between the receiver and the probes,
   wherein the connecting relay board (a) receives input of signal wirings and power distribution lines from n-number, where n is an integer of 2 or more and m≥n, of probes among the m-number of probes, (b) connects the signal wirings from the n-number of probes to the receiver, and (c) connects, to the electrical power source side, the power distribution lines of a number that is fewer than the power distribution lines from the n-number of probes.

2. The object information acquiring apparatus according to claim 1, wherein a plurality of the power distribution lines are connected to each of the probes, and
   wherein the connecting relay board bundles the corresponding power distribution lines between the n-number of probes connected to the connecting relay board.

3. The object information acquiring apparatus according to claim 1, further comprising a scanner moving the detector,
   wherein a positional relation between the detector and the connecting relay board is fixed.

4. The object information acquiring apparatus according to claim 1, wherein a direction in which at least a certain probe among the probes exhibits a highest reception sensitivity differs from the other of the probes.

5. The object information acquiring apparatus according to claim 4, wherein the detector is a semispherical container, and
   wherein directions in which the probes exhibit the highest reception sensitivity extend to a center of a sphere including the semispherical container.

6. The object information acquiring apparatus according to claim 5, wherein the connecting relay board is of a doughnut-like disk shape, and a center of the connecting relay board and a center of the semispherical container are substantially at the same position.

7. The object information acquiring apparatus according to claim 6, wherein the apparatus has a plurality of doughnut-like disk shaped connecting relay boards having different diameters.

8. The object information acquiring apparatus according to claim 1, wherein the apparatus has a plurality of connecting relay boards arranged around the detector.

9. The object information acquiring apparatus according to claim 8, wherein the plurality of connecting relay boards are arranged concentrically.

10. The object information acquiring apparatus according to claim 8, wherein the number of connecting relay boards is from 1 to 16.

11. The object information acquiring apparatus according to claim 1, wherein the connecting relay board includes a plurality of electric circuits that are electrically independent.

12. The object information acquiring apparatus according to claim 1, wherein the connecting relay board includes a local regulator connected to the power distribution line.

13. The object information acquiring apparatus according to claim 1, wherein a connector is used for connection of the probes and the connecting relay board.

14. The object information acquiring apparatus according to claim 13, wherein the connector is mounted on a rear face of the probe.

* * * * *